United States Patent [19]

Takeuchi

[11] Patent Number: 4,966,032

[45] Date of Patent: Oct. 30, 1990

[54] INSTRUMENT FOR TESTING LUBRICATING OIL

[75] Inventor: Kiyoshi Takeuchi, Yokohama, Japan

[73] Assignee: Nissan Motor Co., Ltd., Japan

[21] Appl. No.: 357,886

[22] Filed: May 30, 1989

[30] Foreign Application Priority Data

Jun. 2, 1988 [JP] Japan .................................. 63-72718

[51] Int. Cl.$^5$ ............................................ G01N 33/28
[52] U.S. Cl. ............................................. 73/64; 73/10
[58] Field of Search ............... 73/10, 579, 64, DIG. 4, 73/DIG. 1

[56] References Cited

U.S. PATENT DOCUMENTS

| | | | |
|---|---|---|---|
| 3,739,265 | 6/1973 | Skildum | 324/61 |
| 3,913,377 | 10/1975 | Lindeman | 73/10 |
| 4,311,036 | 1/1982 | Kajdas et al. | 73/10 |
| 4,602,505 | 7/1986 | Kanda et al. | 73/579 |

Primary Examiner—Hezron E. Williams
Assistant Examiner—Rose M. Finley
Attorney, Agent, or Firm—Leydig, Voit & Mayer

[57] ABSTRACT

An instrument for testing the lubricating ability of a lubricating oil has a base member having a contact surface to be submerged in the oil, a vibration member having a friction portion pressed against the contact surface, a driving device having a driving element such as a driving piezoelectric element for vibrating the vibration member, a vibration pickup such as a sensing piezoelectric element for sensing a vibration produced by the friction between the friction portion and the contact surface with the interposition of the lubricating oil, an amplifier for amplifying the output of the pickup, a high-pass filter for filtering the output of the amplifier, and a voltmeter for receiving the output of the filter.

18 Claims, 7 Drawing Sheets

INSTRUMENT FOR TESTING LUBRICATING OIL

BACKGROUND OF THE INVENTION

The present invention relates to an instrument for testing a lubricating ability of a lubricating oil.

FIG. 8 shows a conventional test instrument (as disclosed in a U.S. Pat. No. 3,739,265).

A test instrument 1 of FIG. 8 includes a ring-shaped insulating plate 2, a central electrode 3, and a ring-shaped outer electrode 4. These members are so shaped as to form a liquid resorvoir 5. The bottom of the reservoir 5 is formed by the central electrode 3 and the insulating member 2, and the side wall of the reservoir 5 is formed by the outer electrode 4. The central and outer electrodes 3 and 4 are separated by the insulating member 2, and forms a capacitor, whose capacitance C is measured by a bridge circuit connected with both electrodes by leads 6 and 7. The material contained in the reservoir 5 serves as the dielectric of the capacitor, and the capacitance C is varied by the property of the material. When the lubricating oil is oxidized, or contaminated with sludge, dust, soot, acide etc., then the capacitance C becomes high. When the lubricating oil contains water, coolant or metal particles, then the capacitance becomes extremely high. When gasoline is mixed, the capacitance C becomes low. Therefore, this instrument makes it possible to know the degree of degradation of a lubricating oil by comparing a current capacitance value $C_x$ with an initial capacitance value $C_o$ which was obtained when the oil was new.

However, this conventional instrument is not capable of measuring an absolute value of a lubricating ability. This instrument is arranged to determine the degree of degradation of the oil by measuring a variation from the initial value.

SUMMARY OF THE INVENTION

It is therefore an object of the invention to provide a test instrument which can directly measure the lubricating ability of a lubricating oil.

According to the present invention, an instrument for testing a lubricating oil comprises a supporting means, a friction means, a driving means and a sensing means. The supporting means comprises a base member having a contact surface adapted to be immersed in the lubricating oil. The friction means comprises a vibration member having a friction portion abutting on the contact surface of the base member. The driving means is a means for causing the vibration member to vibrate. The sensing means is a means for sensing a vibration caused by a friction between the friction portion and the contact surface, and producing a sensor output signal.

BRIEF DESCRIPTION OF THE DRAWINGS

FIG. 8 is a sectional view for showing a conventional test instrument.

DETAILED DESCRIPTION OF THE INVENTION

Figure 1:
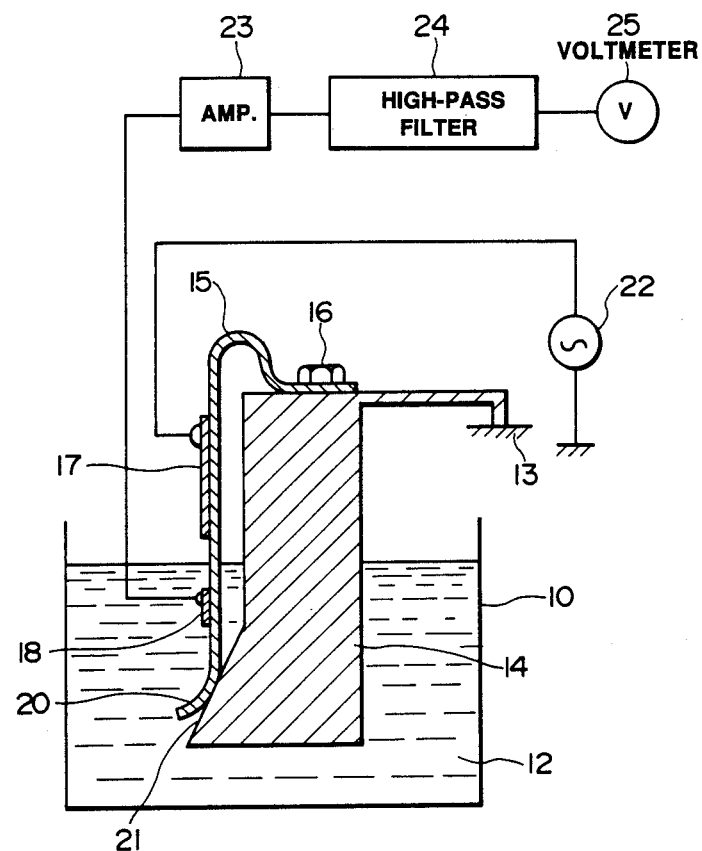
FIG. 1 is a sectional view showing a lubricating oil test instrument according to a first embodiment of the present invention.

A first embodiment of the present invention is shown in FIG. 1.

A lubricating oil tank 10 contains a lubricating oil 12.

A base member 14 is fixed to a support member 13. The base member 14 has an upper portion and a lower portion. The upper portion of the base member 14 of this embodiment has an arm by which the base member 14 is fixed to the support member 13. In the state shown in FIG. 1, the base member 14 extends downwardly from its top end into the tank 10, and the lower portion is immersed in the lubricating oil 12.

A vibration member 15 is fastened to the base member 14 by at least one bolt 16. A driving piezoelectric element 17 and a sensing piezoelectric element 18 are fixedly attached to the vibration member 15. A friction member 20 is fixed to the vibration member 15. In this embodiment, the friction member 20 is an integral part of the vibration member 15. The vibration member 15 is in the form of a plate, and has an upper portion, a lower porton and a middle portion lying between the upper and lower portions. The upper portion of the vibration member 15 is fixed to the top surface of the base member 14 by the bolt 16. The lower portion of the vibration member 15 serves as the friction member 20. The vibration member 15 extends downwardly into the tank 10, and the lower friction portion 20 is immersed in the lubricating oil 12 in the state shown in FIG. 1. The driving and sensing piezoelectric elements 17 and 18 are fixed to the middle portion of the vibration member 15. The friction portion 20 has a chrome plated friction surface facing toward the base member 14.

A contact surface 21 is formed in the lowerportion of the base member 14. The friction surface of the vibration member 15 is in contact with the contact surface 21 of the base member 14 below the surface of the lubricating oil 12. In order to facilitate the contact with the friction surface, the contact surface 21 is inclined so that the contact surface 21 becomes closer to the friction portion 20 toward the lower end of the contact surface 21. The friction portion 20 of the vibration member 15 is curved so that the chrom-plated friction surface is convex, and touches the contact surface 21 along a line or at a point.

The vibration member 15 having the elastic property is anchored only at one end by the bolt 16, and so shaped as to behave as a spring for pushing the friction portion 20 against the contact surface 21. Therefore, the friction portion 20 of the vibration member 15 is always pressed against the contact surface 21. In this embodiment, the upper portion of the vibration member 15 consists of a horizontal flat portion which is fastened to the top of the base member by the bolt 16, and a curved portion which is curved so as to serve as a spring means for pushing the friction portion against the contact surface. The middle portion of the vibration member 15 is substantially flat and vertical.

The driving piezoelectric element 17 is connected with a drive source 22 for producing a periodic drive signal, whose frequency f is set equal to a natural frequency of the vibration member 15. The sensing piezoelectric element 18 is connected with a series circuit of an amplifier 23, a high pass filter 24 and a voltmeter 25.

The friction portion or member 20 of the vibration member 15 and the contact surface 21 of the base member 14 are submerged in the lubrication oil, and the friction portion 20 is always pressed against the contact surface 21 by the spring action of the vibration member 15. When the drive signal of the frequency f is applied to the driving piezoelectric element 15 from the drive source 22, the vibration In this embodiment, the upper portion of the vibration member 15 consists of a horizontal flat portion which is fastened to the top of the base member by the bolt 16, and a curved portion which is curved so as to serve as a spring means for pushing the friction portion against the contact surface member 15 is vibrated with the frequency f by being expanded and contracted repeatedly. Accordingly, the friction portion 20 of the vibration member 15 moves back and forth relative to the contact surface 21 of the base member 14, and the friction surface of the friction portion 20 rubs on the contact surface 21.

Figure 2A:
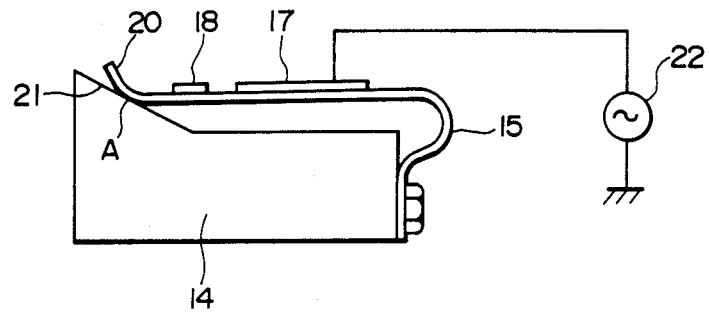
FIGS. 2A, 2B and 2C are sectional views for illustrating movement of a vibration member shown in FIG. 1 exaggeratingly.
Figure 2B:
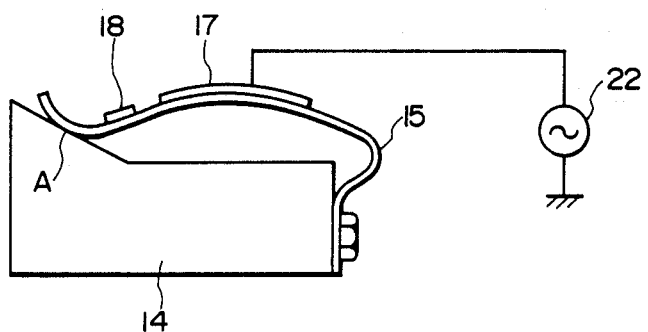
Figure 2C:
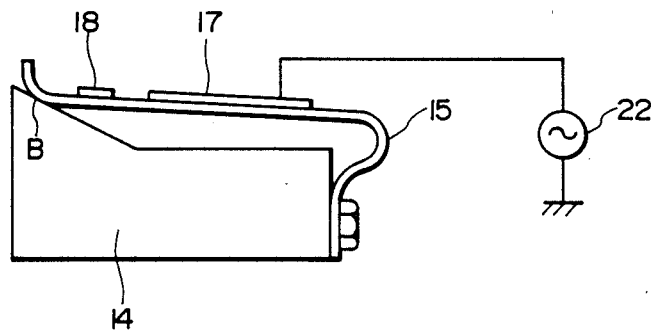

FIGS. 2A, 2B and 2C show movement of the vibration member 15 in an exaggerated manner. When no voltage is applied to the driving piezoelectric element 17, the friction portion 20 of the vibration member 15 is in contact with the contact surface 21 at a point A as shown in FIG. 2A. If we assume a DC voltage V is applied to the driving piezoelectric element 17 from the drive source 22, then the vibration member 15 grows longer together with the driving piezoelectric element 17 by the piezoelectric effect. However, the friction force between the frictional portion 20 and the contact surface 21 temporarily prevents the friction portion 20 from moving relative to the contact surface 21, so that the point of contact remains at the point A, and the middle portion of the vibration member 15 bulges outwardly, as exaggeratedly shown in FIG. 2B. If a force applied to the friction portion 20 by the expansion of the vibration member 15 exceeds a limiting value, then the friction portion 20 starts sliding on the contact surface 21, and the point of contact between the friction portion 20 and the contact surface 21 moves, as shown in FIG. 3C, from the point A to a point B until an equilibrium state is reached. This limiting value is determined by the lubricating ability of the lubricating oil 12. In this embodiment, the drive source 22 is arranged to apply a periodically changing voltage signal, such as an alternating voltage, to the driving piezoelectric element 17. Therefore, the point of contact between the friction portion 20 and the contact surface 21 vibrates along the contact surface 21 by the action of the periodic voltage applied to the driving piezoelectric element 17, and at the same time fluctuates minutely by the action of the friction between the friction portion 20 and the contact surface 21. As a result, the vibration of the vibration member 15 has a fundamental waveform of the exciting frequency f, and a waveform of a higher frequency caused by the friction between the friction portion 20 and the contact surface 21.

Figure 3A:
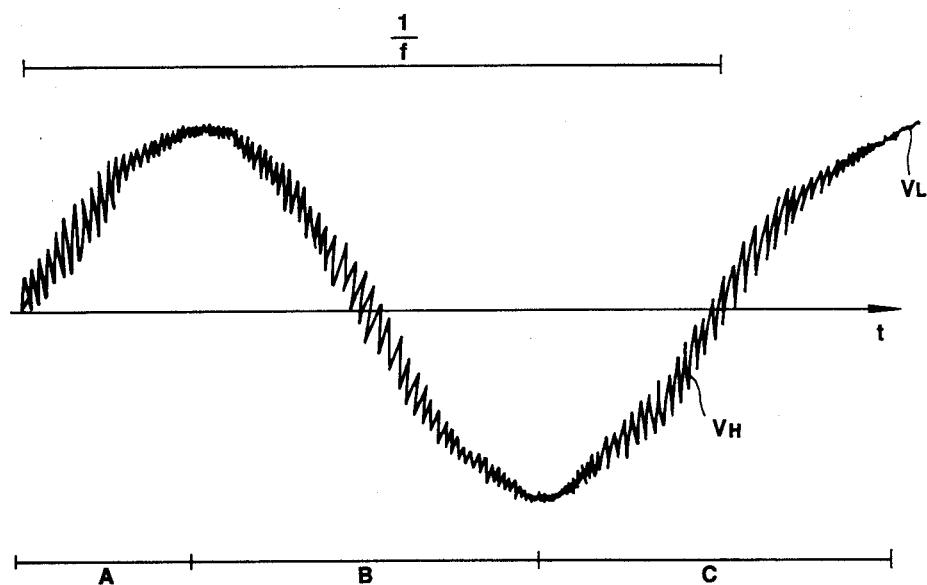
FIGS. 3A and 3B are diagrams showing waveforms of signals appearing in the test instrument of FIG. 1.

The sensing piezoelectric element 18 responds to the vibration occurring in the vibration member 15, and produces a voltage signal as shown in FIG. 3A. In the period A in FIG. 3A, the sensing piezoelectrc element 18 is sensing movement of the friction portion 20 caused by a change of the vibration member 15 from the state in which no voltage is applied to the driving piezoelectric element 17 and accordingly the vibration member 15 is neither expanded nor compressed, to the state in which the vibration member 15 is elongated by the application of a voltage to the driving piezoelectric element 17. The vibration member 15 is compressed in the next period B, and elongated again in the period C.

Figure 3B:
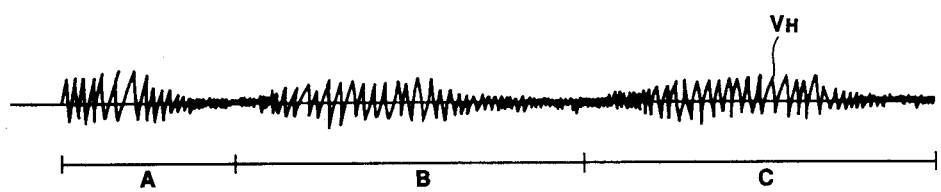

The amplifier 23 amplifies the output signal of the sensing element 18. The high-pass filter 24 receives the output signal of the amplifier 23, and delivers an output signal as shown in FIG. 3B, to the voltmeter 25. The high-pass filter 24 is a filter which prevents the passage of a low frequency oscillation $V_L$, having the frequency f of the drive source 22, and allows the passage of a high frequency oscillation $V_H$ produced by the friction between the friction portion 20 and the contact surface 21. Therefore, only the high frequency oscillation $V_H$ is inputted to the voltmeter 25, as shown in FIG. 3B. This high frequency oscillation $V_H$ is derived from the vibration of the vibration member 15 caused by the friction between the friction portion 20 and the contact surface. Therefore, the voltage indicated by the voltmeter 25, that is the magnitude of the vibration due to the friction, is indicative of the friction force between the friction portion 20 and the contact surface 21. When the friction force becomes greater because of the degradation of the lubricating oil 12, then a vibration of a higher amplitude is produced in the vibration member 15, and accordingly the voltmeter 25 indicates a higher voltage. In this way, the voltage measured by the voltage meter 25 represents the lubricating characteristic of the lubricating oil 12.

Figure 4:
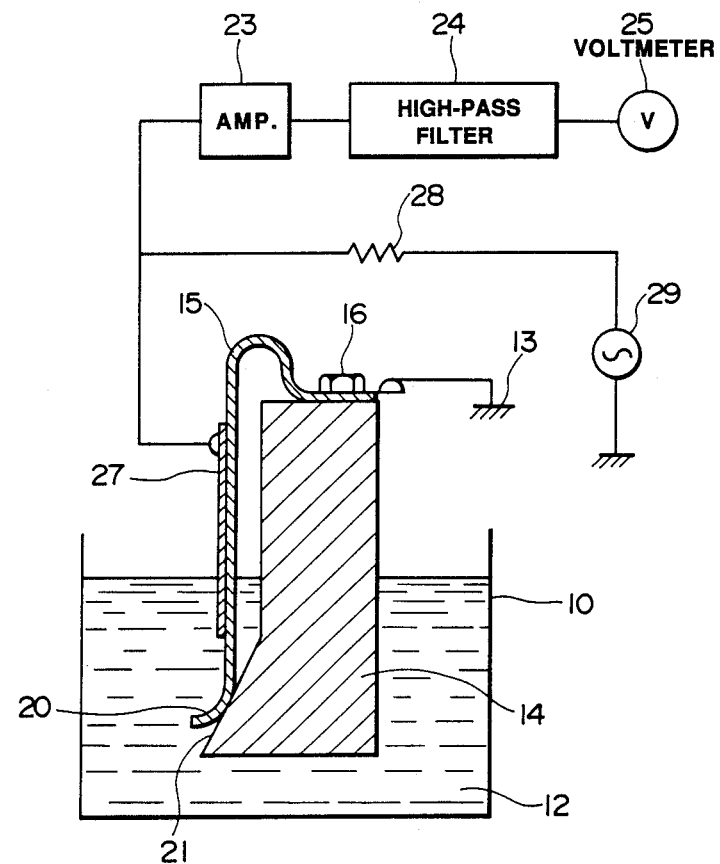
FIG. 4 is a sectional view of a test instrument according to a second embodiment of the present invention.

A second embodiment of the invention is shown in FIG. 4.

A test instrument of the second embodiment is almost the same as that of the first embodiment. Like the instrument shown in FIG. 1, the test instrument shown in FIG. 4 includes the support member 13, base member 14, vibration member 15, amplifier 23, high-pass filter 24 and voltmeter 25.

However, the test instrument of FIG. 4 is different from that of the first embodiment in the following points. The instrument of the second embodiment employs a single piezoelectric element 27 in place of the driving and sensing piezoelectric elements 17 and 18 of the first embodiment. The piezoelectric element 27 is fixed to the vibration member 15. The piezoelectric element 27 is connected to a drive source 29 via a resistor 28 on one hand. On the other hand, the piezoelectric element 27 is further connected to the voltmeter via the amplifier 23 and the high-pass filter 24.

Like the driving piezoelectric element 17 of the first embodiment, the piezoelectric element 27 of the second embodiment forces the vibration member 15 to vibrate when the alternating voltage is applied by the drive source 29. At the same time, the piezoelectric element 27 picks up the vibration produced in the vibration member 15, and delivers the signal similar to the signal shown in FIG. 3A, to the high-pass filter 24 via the amplifier 23. The buffer resistor 28 makes it possible to send the output signal of the piezoelectric element 27 correctly to the amplifier 23 notwithstanding the existence of the branch toward the drive source 29.

Figure 5:
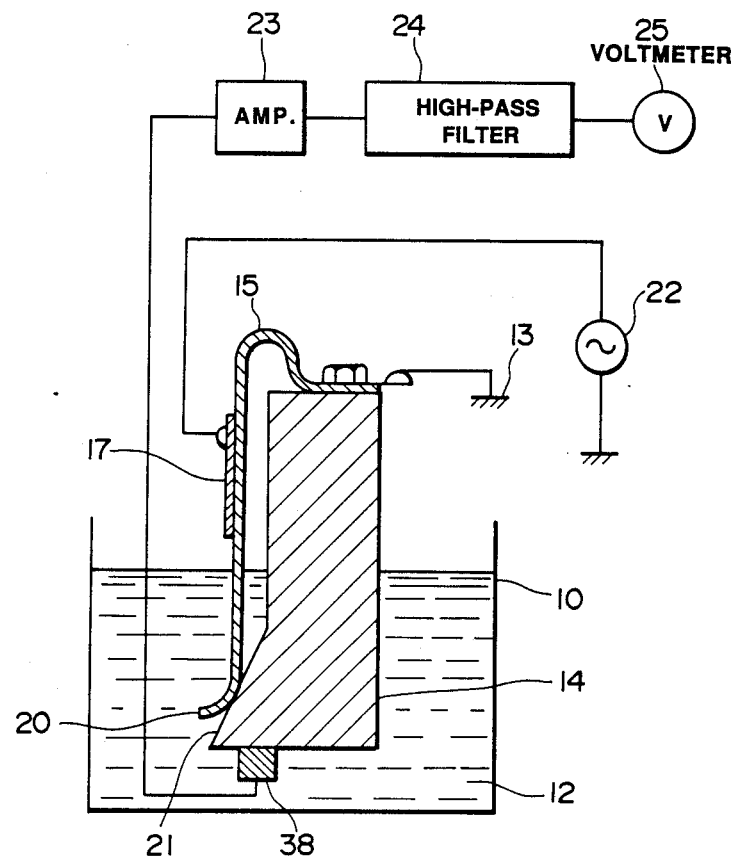
FIG. 5 is a sectional view of a test instrument according to a third embodiment of the present invention.

A third embodiment of the present invention is shown in FIG. 5. In the third embodiment, the sensing piezoelectric element 18 employed in the first embodiment is replaced by a vibration pickup 38 attached to the base member 14. The vibration pickup 38 is connected with the voltmeter 25 via the amplifier 23 and the high-pass filter 24. The vibration pickup 38 is designed to sense the friction force between the friction portion 20 and the contact surface 21 by sensing a vibration produced in the base member 14. In the other respects, the instrument of the third embodiment is the same as that of the first embodiment.

In this way, the instrument of each of the preceding embodiments is arranged to sense the lubricating ability of the lubricating oil by sensing the amplitude of the vibration caused by the friction which is proportional to the magnitude of the friction force. Therefore, the instrument of the invention can provide the absolute value of the lubricating ability of the oil. Furthermore, the test instrument of the invention makes it possible to measure the grade of an oil within an oil tank without taking a sample out of the tank.

Figure 6:
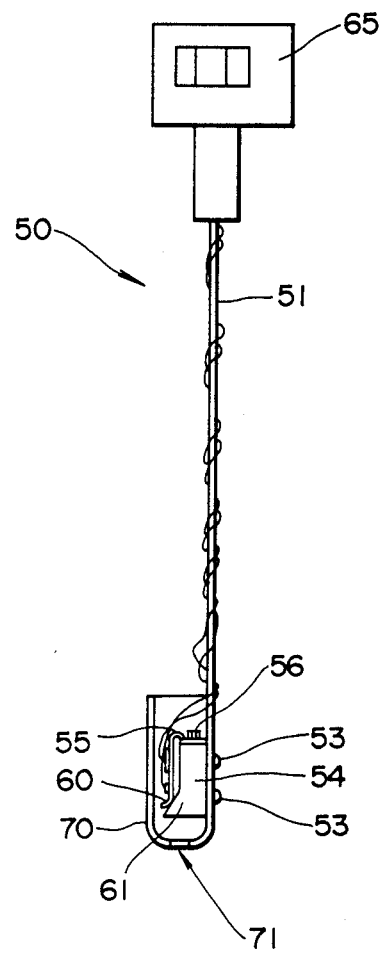
FIG. 6 is a view of a test instrument according to a fourth embodiment of the present invention.

FIG. 6 shows a fourth embodiment of the present invention, in which the test instrument of the first, second or third embodiment is incorporated into an oil level gauge 50.

Figure 7:
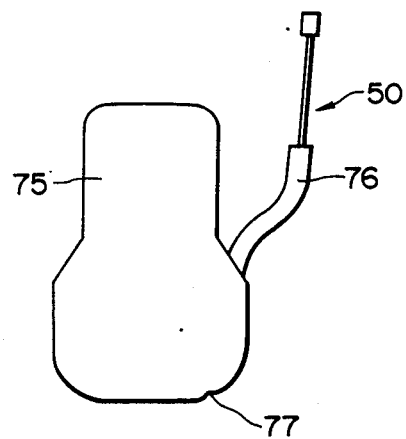
FIG. 7 is an elevation of an engine for illustrating usage of the test instrument of the fourth embodiment.
Figure 7:
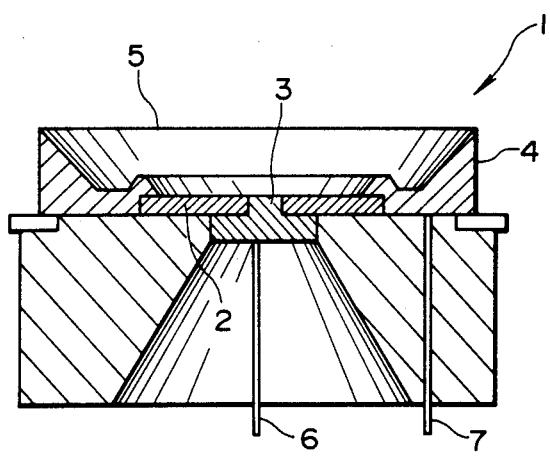

An instrument 50 in the form of the oil level gauge has a rod 51 extending from an upper end to a lower end. A base member 54 similar to the base member 14 is fixed to the lower end of the rod 51 by bolts 53. A vibration member 55 similar to the vibration member 15 is fixed to the base member 54 by at least one bolt 56. A friction portion 60 of the vibration member 55 is pushed against, and held in contact with a contact surface 61 formed in the base member 54 in the same manner as in the preceding embodiments. The base member 54 and the vibration member 55 are enclosed in a protective case 70. A hole 71 is formed at the bottom of the protective case 70 for introducing oil into the inside of the case 70. A unit 65 including the boltmeter 25 and other circuit components is fixed to the upper end of the rod 51. As shown in FIG. 7, the test instrument 50 of the fourth embodiment is inserted into an oil pan 77 through an oil level gauge hole 76 of an engine 75 of a motor vehicle or some other machine, and used for measuring the oil level, and the degree of degradation of the oil.

In the present invention, it is possible to employ some other vibration detecting device instead of the combination of the amplifier, high-pass filter and voltmeter. It is further possible to employ some other vibrator instead of the piezoelectric element for vibrating the vibration member. It is possible to mount the test instrument of the first, second or third embodiment in an engine to always monitor the property of the engine lubricating oil.

The test instrument of the present invention is so compact that the measurement becomes very easy, and accurate in that it can directly sense the lubricating ability of the oil in the condition similar to the actual working condition.

What is claimed is:

1. An instrument for testing a lubricating oil, comprising;
   supporting means comprising a base member having a contact surface adapted to be immersed in said lubricating oil,
   friction means comprising a vibration member having a friction portion abutting on said contact surface,
   driving means for causing said vibration member to vibrate, and
   sensing means for sensing a vibration caused by a friction between said friction portion and said contact surface, and producing a sensor output signal.

2. An instrument according to claim 1 wherein said sensing means comprises filter means for attenuating frequency components of said sensor output signal in a predetermined frequency band.

3. An instrument according to claim 2 wherein said driving means applies a periodic driving force of a predetermined exciting frequency to said vibration member, and said filter means comprises a filter capable of attenuating said exciting frequency.

4. An instrument according to claim 3 wherein said filter is a high-pass filter.

5. An instrument according to claim 4 wherein said driving means comprises a driving piezoelectric element attached to said vibration member, and a periodic voltage source for applying a periodic voltage signal to said driving piezoelectric element.

6. An instrument according to claim 5 wherein said sensing means further comprises a voltmeter connected with said high-pass filter.

7. An instrument according to claim 6 wherein said sensing means comprises a sensing element attached to one of said vibration member and said base member.

8. An instrument according to claim 7 wherein said sensing element is a sensing piezoelectric element attached to said vibration member.

9. An instrument according to claim 8 wherein said friction means comprises spring means for pushing said friction portion against said contact surface.

10. An instrument according to claim 9 wherein said base member has an upper portion and a lower portion in which said contact surface is formed, and said vibration member is in a form of a plate, and has an upper portion fastened to said upper portion of said base member, a middle portion extending downwardly from said upper portion of said vibration member, and said friction portion which extends downwardly from said middle portion.

11. An instrument according to claim 10 wherein said friction portion of said vibration member is curved, and has a convex surface abutting on said contact surface of said base member.

12. An instrument according to claim 11 wherein said middle portion of said vibration member is substantially flat and extends in a vertical plane, and said contact surface of said base member is inclined so that said contact surface intersects said vertical plane.

13. An instrument according to claim 12 wherein said driving piezoelectric element is attached to said middle portion of said vibration member so that said driving piezoelectric element can increase and decrease a vertical length of said middle portion.

14. An instrument according to claim 13 wherein said sensing means further comprises an amplifier connected between said sensing piezoelectric element and said high-pass filter.

15. An instrument according to claim 7 wherein said sensing element is attached to said base member.

16. An instrument according to claim 6 wherein said driving piezoelectric element is connected to a node which is connected to said voltage source through a buffer resistor, and which is further connected to said high-pass filter.

17. An instrument according to claim 6 wherein said supporting means comprises a protective case enclosing said base member and said vibration member, and said base member is fixed to said protective case.

18. An instrument according to claim 17 wherein said supporting means further comprises a rod for serving as an oil level gauge, said rod having an upper end and a lower end, said protective case being fixed to said lower end of said rod, and said voltmeter being mounted on said upper end of said rod.

* * * * *